(12) United States Patent
Iselborn et al.

(10) Patent No.: US 9,011,790 B2
(45) Date of Patent: Apr. 21, 2015

(54) REACTOR FOR PERFORMING A THREE-PHASE REACTION OF A FLUID AND A GASEOUS PHASE ON A PACKED BED CATALYST

(75) Inventors: Stefan Iselborn, Frankenthal (DE); Andreas Daiss, Deidesheim (DE); Reiner Geier, Mannheim (DE); Marcus Bechtel, Heidelberg (DE); Michael Wille, Mannheim (DE); Benjamin Hepfer, Mannheim (DE); John Sauter, Bloomfield, NJ (US)

(73) Assignee: BASF SE, Ludwigshafen (DE)

( * ) Notice: Subject to any disclaimer, the term of this patent is extended or adjusted under 35 U.S.C. 154(b) by 1193 days.

(21) Appl. No.: 12/665,533

(22) PCT Filed: Jun. 20, 2008

(86) PCT No.: PCT/EP2008/057832
§ 371 (c)(1),
(2), (4) Date: Dec. 18, 2009

(87) PCT Pub. No.: WO2008/155399
PCT Pub. Date: Dec. 24, 2008

(65) Prior Publication Data
US 2010/0185032 A1     Jul. 22, 2010

Related U.S. Application Data

(60) Provisional application No. 60/945,461, filed on Jun. 21, 2007.

(51) Int. Cl.
*B01J 8/02*      (2006.01)
*B01J 8/04*      (2006.01)
*C07C 7/167*    (2006.01)
*B01J 8/00*      (2006.01)
*B01J 19/00*    (2006.01)
*B01J 19/24*    (2006.01)
*B01J 19/30*    (2006.01)
*B01J 35/00*    (2006.01)
*B01J 35/02*    (2006.01)

(52) U.S. Cl.
CPC  *B01J 8/008* (2013.01); *B01J 8/025* (2013.01); *B01J 8/0278* (2013.01); *B01J 8/0453* (2013.01); *B01J 8/0492* (2013.01); *B01J 2208/00548* (2013.01); *C07C 7/167* (2013.01); *C10G 2400/20* (2013.01)

(58) Field of Classification Search
CPC ........ B01J 19/00; B01J 19/0093; B01J 19/32; B01J 7/00; B01J 8/00; B01J 8/1827; B01J 8/1818; B01J 8/0278; B01J 8/0453; B01J 8/0492; B01J 8/025; B01J 2523/00; B01J 35/023; B01J 2219/3221; B01J 2219/32213; B01J 2219/32227; B01J 2219/32408; B01J 2219/00006; B01J 8/02; B01J 8/0242; B01J 19/24; B01J 19/30; B01J 35/00; B01J 35/02; B01J 2208/00008; B01J 2208/00548; B01J 2208/00796; B01J 2208/00893; B01J 2208/00902; B01J 2208/00911; B01J 2208/0092; B01J 2208/00929; B01J 2208/0093; C07C 15/08; C07C 4/06; C07C 7/04; C07C 7/12; C07C 19/075; C07C 45/50; C07C 51/265; C07C 67/08; C01B 2203/0233; C08F 10/00; Y10S 261/11; F28C 1/14; F28C 1/00; F28C 1/02; B01D 53/18; B01D 3/20; B01D 3/22; B01D 3/324; B01D 3/008; B01D 3/009; B01D 3/163; B01D 3/205
USPC ......... 422/129, 139, 187, 211, 220, 224, 310, 422/600, 606, 607, 630, 632, 644, 647; 261/109–111, 112.1, 112.2, 113, 261/114.1–114.5
See application file for complete search history.

(56) References Cited

U.S. PATENT DOCUMENTS

| | | | | |
|---|---|---|---|---|
| 2,898,292 A | * | 8/1959 | Halik et al. | 208/250 |
| 3,146,189 A | * | 8/1964 | Kunreuther et al. | 208/146 |
| 3,502,445 A | * | 3/1970 | Hines, Jr. et al. | 422/607 |
| 3,541,000 A | * | 11/1970 | Hanson et al. | 208/108 |
| 4,557,877 A | * | 12/1985 | Hofstetter | 261/97 |

| | | | |
|---|---|---|---|
| 4,808,350 A | | 2/1989 | Robbins et al. |
| 4,836,989 A | * | 6/1989 | Aly et al. ............... 422/605 |
| 4,937,051 A | * | 6/1990 | Graven et al. ........... 422/106 |
| 5,232,283 A | | 8/1993 | Goebel et al. |
| 5,246,568 A | * | 9/1993 | Forbus et al. ............ 208/59 |
| 5,484,518 A | | 1/1996 | Goldberg |
| 5,484,578 A | | 1/1996 | Muldowney et al. |
| 5,817,901 A | | 10/1998 | Trambouze et al. |
| 6,613,219 B2 | | 9/2003 | Harter et al. |
| 6,669,915 B1 | | 12/2003 | Boyd et al. |
| 7,250,142 B2 | * | 7/2007 | Boyer et al. ............. 422/606 |
| 7,611,683 B2 | | 11/2009 | Grund et al. |
| 2002/0172632 A1 | * | 11/2002 | Chou ...................... 422/220 |
| 2005/0062178 A1 | | 3/2005 | Harter et al. |
| 2006/0163758 A1 | | 7/2006 | Muller |

FOREIGN PATENT DOCUMENTS

| | | |
|---|---|---|
| DE | 102004021128 A1 | 11/2005 |
| EP | 1147809 A1 | 4/2001 |
| GB | 1274327 | 5/1972 |
| WO | WO-95/35159 A1 | 12/1995 |
| WO | WO-03/039733 A1 | 5/2003 |

* cited by examiner

*Primary Examiner* — Natasha Young

(74) *Attorney, Agent, or Firm* — Drinker Biddle & Reath LLP

(57) ABSTRACT

A reactor for carrying out a three-phase reaction of a liquid phase, a gaseous phase, and a catalyst over a fixed catalyst bed is disclosed. The liquid and gaseous phases are passed through the reactor via a mixing and distribution device positioned over the fixed catalyst bed. The mixing and distribution device includes a trough distributor for the liquid phase, having trough-shaped channels, outlet tubes in the trough-shaped channels for the liquid phase, a distributor plate below the trough distributor, and vertical nozzles, having one or more openings for the gaseous phase and one or more openings, arranged below the openings for the gaseous phase. For entry of the liquid phase, the nozzles are installed so that, at a predetermined liquid feed rate, the surface of the liquid on the distributor plate is below the openings for the gaseous phase and above the openings for the liquid phase.

15 Claims, 2 Drawing Sheets

Figure 1:
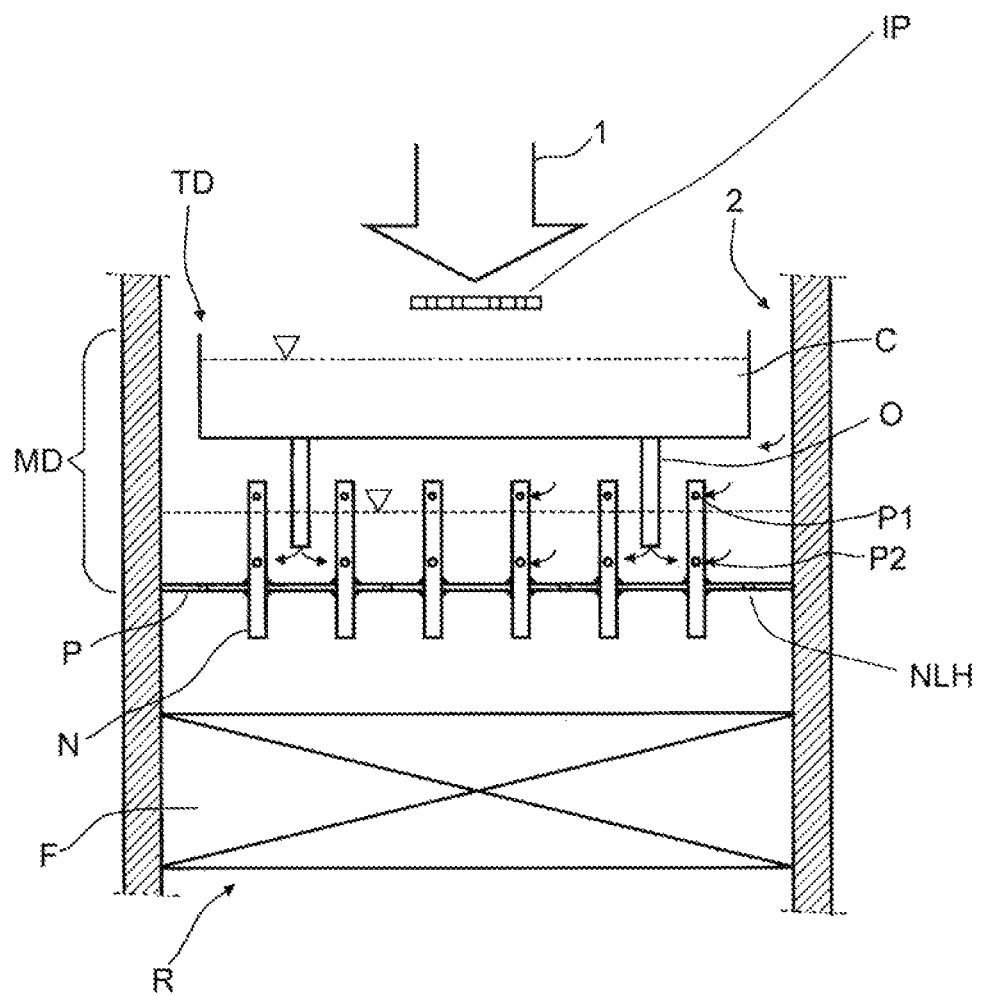

REACTOR FOR PERFORMING A THREE-PHASE REACTION OF A FLUID AND A GASEOUS PHASE ON A PACKED BED CATALYST

Priority is claimed as a national stage application, under 35 U.S.C. §371, to PCT/EP2008/057832, now WO 2008/155399, filed Jun. 20, 2008, which claims priority to U.S. Provisional application 60/945,461, filed Jun. 21, 2007. The disclosures of the aforementioned priority applications are incorporated herein by reference in their entirety.

The invention relates to a reactor for carrying out a three-phase reaction of a liquid phase and a gaseous phase over a fixed catalyst bed, having a mixing and distribution device for the liquid phase and the gaseous phase, a process for carrying out three-phase reactions and a use.

Three-phase reactions of a liquid phase and a gaseous phase over a fixed catalyst bed are frequent in chemical processing engineering. A mode of operation using one or more fixed catalyst beds which are arranged horizontally in an upright reactor and over which the liquid phase and the gaseous phase are passed is often used for this purpose. Conversion and selectivity of the reactions which occur depend not only on the reaction kinetics but also, in particular, on the hydrodynamics of the reactor. Uniform progress of the reaction is necessary for this purpose, and this in turn requires that both the gas and the liquid, i.e. both reactants, are optimally very uniformly distributed both in the radial direction and in the axial direction in the reactor. This is problematical in, in particular, large industrial reactors having correspondingly large dimensions.

In addition, three-phase reactors are usually operated adiabatically, i.e. the temperature changes as the conversion progresses as a consequence of the heat of reaction liberated or taken up and accordingly increases or decreases due to the lack of external heat exchange. To achieve a homogeneous temperature distribution without hotspots and thus without corresponding disadvantageous effects, in particular on the operating life of the catalyst, on conversion and selectivity, uniform distribution of the starting materials is likewise desirable.

For this reason, many devices for ensuring a very homogenous distribution of a liquid phase and a gaseous phase on the surface of a fixed catalyst bed have been developed in chemical processing engineering.

U.S. Pat. No. 5,817,901 describes a process for the selective hydrogenation of hydrocarbon fractions having from 2 to 20 carbon atoms per molecule over a fixed-bed catalyst, in which the hydrocarbon stream and hydrogen are fed to the fixed bed via a static mixer of the SMV or SMX type from Sulzer, upstream of which a liquid distributor which is not described in more detail is advantageously located. For example, selective hydrogenations of butadiene to 1-butenes from a C4 fraction are described for a reactor having a diameter of 10 cm, with selectivities of not more than about 58% being achieved for the above conversion of butadiene into 1-butenes. However, satisfactory selectivities for the selective hydrogenation of acetylenic and dienic components from hydrocarbon fractions cannot be achieved in industrial reactors purely by means of the combination of a static mixer, for example of the SMV or SMX type from Sulzer and a liquid distributor which is not specified in more detail.

EP-A 1 147 809 describes a distributor for a polyphase mixture comprising at least one gaseous phase and at least one liquid phase onto a fixed bed, which is made up of a distributor plate on which outlet tubes are arranged and at whose lower end a further distributor element in the form of a sieve is provided.

WO-A 03/039733 describes a distributor for a mixture comprising at least one gaseous phase and at least one liquid phase onto a fixed bed. The distributor comprises a distributor plate P which is provided with a plurality of mixing and outlet tubes through the plate which have an upper inlet opening for the gas, lateral inlet openings for the liquid and, if appropriate, a small part of the gaseous phase and a lower opening for the mixture of gaseous and liquid phases, with an additional distributor element in the form of a sieve having a controlled porosity and upturned side walls being arranged below the lower opening and above a fixed catalyst bed. The arrangement of the additional distributor element ensures more uniform flow of gaseous and liquid phases onto the fixed catalyst bed compared to an embodiment without this.

WO-A 95/35159 describes a further two-phase distributor for a gaseous phase and a liquid phase onto a fixed bed, which has a distributor plate and outlet tubes, with two groups of outlet tubes having openings at different heights being provided so that uniform distribution is ensured even at low throughputs.

DE-A 10 2004 021 128 describes a further reactor having an inlet for a gaseous starting material and a liquid starting material in cocurrent to a fixed-bed catalyst, with a distributor plate having openings with static mixers arranged in the openings being provided upstream of this. The combination of distributor plate and static mixers enables a significant decrease in the aspect ratio h/d, i.e. the ratio of height to diameter of the reactor, to values of <5 to be achieved.

However, conversions and selectivities of three-phase reactions, in particular selective hydrogenations, in large industrial reactors having diameters of greater than 0.5 m have not been satisfactory when using the known distributor devices.

It was therefore an object of the invention to provide a mixing and distribution device for a three-phase reactor which can be scaled up and ensures a largely uniform distribution of the gaseous phase and the liquid phase and thus high conversions and selectivities, even in the case of large industrial reactors.

The object is achieved by a reactor for carrying out a three-phase reaction of a liquid phase and a gaseous phase over a fixed catalyst bed, with the fixed catalyst bed being arranged horizontally in the reactor and the liquid phase and the gaseous phase being passed through the reactor in cocurrent from the top downward via a mixing and distribution device over the fixed catalyst bed, wherein the mixing and distribution device comprises a trough distributor for the liquid phase having trough-shaped channels and outlet tubes in the trough-shaped channels for the liquid phase and a distributor plate which is arranged with a spacing below the trough distributor and in which vertical nozzles having one or more openings for entry of the gaseous phase and one or more openings, which are arranged below the openings for entry of the gaseous phase, for entry of the liquid phase into the nozzles are installed, with the number and size of the openings for entry of the liquid phase being designed so that, at a predetermined liquid feed rate, the surface of the liquid on the distributor plate is established below the openings for entry of the gaseous phase and above the openings for entry of the liquid phase.

The invention accordingly provides a mixing and distribution device for a liquid phase and a gaseous phase, which comprises two main parts, viz. a distributor for the liquid phase which is, in a manner analogous to known trough distributors, equipped with trough-shaped channels in which outlet tubes for the liquid phase are installed, but with the particular feature that the outlet tubes extend to the vicinity of the distributor plate which functions as main distributor and is arranged underneath so that the outlet tubes always dip into the liquid which stands on the distributor plate. For this purpose, vertical nozzles which have one or more openings for entry of the gaseous phase and one or more openings arranged below these for entry of the liquid phase are installed in the distributor plate, with the number and size of the openings for entry of the liquid phase being designed so that, at a predetermined liquid feed rate, the surface of the liquid on the distributor plate is established below the openings for entry of the gaseous phase and above the openings for entry of the liquid phase.

As a result of the outlet tubes of the predistributor always extending below the surface of the liquid on the distributor plate functioning as main distributor, the liquid flowing out via the outlet tubes from the trough distributor functioning as predistributor is always introduced uniformly into the liquid standing on the distributor plate without the liquid exiting as a jet or even squirting.

The number and size of the openings for entry of the liquid phase into the nozzles of the distributor plate are preferably designed so that the surface of the liquid on the distributor plate is established below the openings for entry of the gaseous phase and above the openings for entry of the liquid phase even in the case of deviations of the liquid feed rate from the predetermined liquid feed rate by up to 20% in an upward direction and by up to 50% in a downward direction.

According to the invention, uniform distribution of liquid and gaseous phases is ensured, in particular also for large reactors having a diameter in the range from 0.5 to 5 m or in the range from 1 to 4 m or in the range from 1.2 to 3 m.

Preference is given to from 50 to 200 or from 70 to 150 or from 90 to 130 nozzles per $m^2$ being arranged regularly on the distributor plate which functions as main distributor.

Here, the nozzles can be arranged in triangular positions or in a square arrangement on the distributor plate.

The nozzles preferably have a free diameter of from 5 to 75 mm, a length of from 100 to 600 mm above the distributor plate and a length of from 20 to 250 mm below the distributor plate and have openings for entry of the liquid phase having a diameter of from 2 to 45 mm or from 20 to 45 mm which are arranged at a height of from 10 to 100 mm above the distributor plate and also openings for entry of the gaseous phase having a diameter of from 1 to 30 mm.

The nozzles more preferably have a free diameter of from 10 to 60 mm, a length of from 200 to 400 mm above the distributor plate and a length of from 50 to 200 mm below the distributor plate and also openings for entry of the liquid phase having a diameter of from 3 to 35 mm at a height of from 22 to 75 mm above the distributor plate and openings for entry of the gaseous phase having a diameter of from 5 to 20 mm.

The nozzles more preferably have a free diameter of from 35 to 50 mm, a length of from 250 to 350 mm above the distributor plate and a length of from 100 to 150 mm below the distributor plate and also openings for entry of the liquid phase having a diameter of from 10 to 25 mm which are arranged at a height of from 40 to 60 mm above the distributor plate and openings for entry of the gaseous phase having a diameter of from 5 to 15 mm or from 7 to 15 mm.

The openings for entry of the liquid phase can advantageously be adjusted in respect of their height and orientation.

The pressure drop of the gaseous phase between entry into the reactor and entry into the nozzles is preferably controlled via the number and openings for entry of the gaseous phase so that the pressure drop of the gaseous phase between entry into the reactor and entry into the nozzles at the lowest gas throughput in operation of the reactor is from 50 to 500 pascal, preferably from 75 to 300 pascal, more preferably from 100 to 200 pascal.

The reactor of the invention is preferably operated continuously.

To be able to empty the reactor in the case of necessary interruptions to operation, the distributor plate is provided with no-load holes which are distributed uniformly over the distributor plate and whose number and size is selected so that in normal operation of the reactor only a maximum of 5% of the total liquid phase passed through the reactor flows through the no-load holes.

The no-load holes preferably have a diameter in the range from 10 to 20 mm.

The trough distributor functioning as predistributor, which has trough-shaped channels having outlet tubes in the trough-shaped channels for the liquid phase, is preferably configured so that the trough-shaped channels comprise a main channel and two or more side channels which are configured so that the liquid phase can flow unhindered between the main channel and the side channels.

In particular, main channel and side channels are configured relative to one another in such a way that the sum of the base areas of the main channel and the side channels is from 30 to 70%, preferably from 40 to 60%, of the total cross-sectional area of the reactor.

The trough-shaped channels of the trough distributor preferably have a height of from 200 to 600 mm, particularly preferably from 250 to 500 mm, more preferably from 300 to 400 mm. The trough distributor is also arranged from 10 to 300 mm, preferably from 20 to 200 mm, above the upper end of the nozzles.

Preference is given to from 30 to 120, more preferably from 40 to 100, particularly preferably from 50 to 80, openings per $m^2$ having a diameter of from 5 to 40 mm, particularly preferably from 10 to 35 mm, more preferably from 15 to 25 mm, being provided at the bottom of the trough-shaped channels, with an outlet tube having a diameter of from 15 to 75 mm, preferably from 25 to 60 mm, more preferably from 35 to 50 mm, being installed at each opening and the length of the outlet tubes being set so that the lower end of these is from 20 to 200 mm, preferably from 25 to 150 mm, above the distributor plate.

A further improved uniform distribution is achieved by a preferred embodiment of the reactor in which the liquid phase introduced into the reactor via an inlet tube impinging on an impingement plate in the form of a disk having orifices at the end of the inlet tube at which the liquid phase enters the reactor and at a distance of a few centimeters from the end of the inlet tube.

The invention also provides a process for carrying out a three-phase reaction between a liquid phase and a gaseous phase over a fixed catalyst bed in a reactor, with the fixed catalyst bed being arranged horizontally in the reactor and the liquid phase and the gaseous phase being passed through the reactor in cocurrent from the top downward via a mixing and distribution device over the fixed catalyst bed, wherein the liquid phase is introduced from outside the reactor via an inlet tube into a trough distributor having trough-shaped channels and outlet tubes in the trough-shaped channels and the gaseous phase is introduced separately or together with the liquid phase via a port which is arranged upstream of the distributor plate into a gas space between the trough distributor and a distributor plate which is arranged with a spacing below the trough distributor and in which vertical nozzles are installed, with the liquid phase being introduced via the outlet tubes of the trough distributor below the surface of the liquid into the liquid standing on the distributor plate and the gaseous phase being introduced via one or more openings from the gas space into the nozzles of the distributor plate and the liquid phase being fed via one or more openings below the surface of the liquid into the nozzles on the distributor plate and the mixture of liquid phase and gaseous phase being fed via the nozzles to the fixed catalyst bed.

The invention also provides for the use of the above-described reactor or the above-described process for carrying out a selective hydrogenation of hydrocarbon fractions. Preference is given to a use in which the hydrocarbon fractions are C2, C3 or C4 hydrocarbon fractions or pyrolysis gases.

The hydrocarbon fractions are particularly preferably C4 fractions, with butadiene in the C4 fractions being selectively hydrogenated to n-butenes. The use of the reactor of the invention having a specific configuration of the predistributor and of the main distributor makes it possible to hydrogenate 1,3-butadiene virtually quantitatively to n-butenes and to avoid overhydrogenation to butane.

The invention is illustrated below with the aid of a figure and of examples.

FIG. 1 schematically shows a longitudinal section through a reactor R with introduction of the liquid phase 1 and the gaseous phase 2 from above in each case via ports which are not shown.

Figure 2:
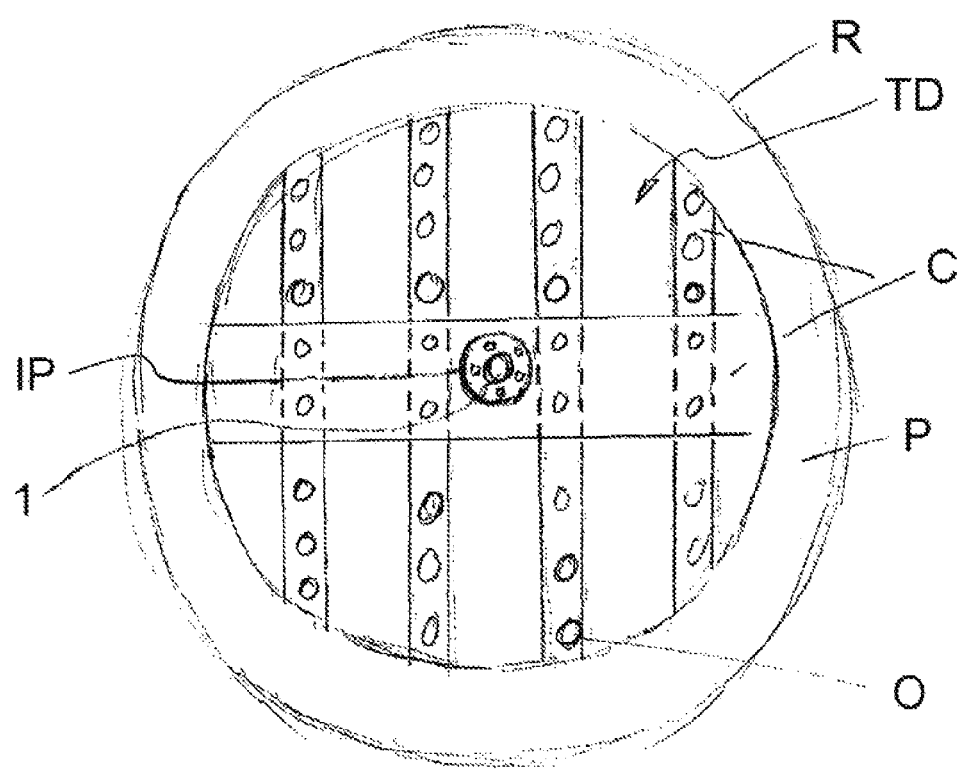

FIG. 2 schematically shows an axial section though the reactor r shown in FIG. 1.

In the reactor R, a mixing and distribution device MD which has a predistributor configured as a trough distributor TD having outlet tubes O arranged on its bottom and a distributor plate P which is located downstream of the trough distributor TD and functions as main distributor is arranged above a fixed catalyst bed F. Nozzles N which project above and below the distributor plate P into the interior of the reactor R are installed in the distributor plate P. In the region of the nozzles N above the distributor plate P, openings P1 are provided above the surface of the liquid on the distributor plate P for entry of the gaseous phase 2 and openings P2 are provided below the surface of the liquid on the distributor plate P for entry of the liquid phase 1. The distributor plate is provided with no-load holes NLH.

FIG. 1 also schematically shows how the liquid phase can be introduced into the reactor via an inlet which can impinge on an impingement plate IP. The impingement plate IP is in the form of a disk and includes orifices that can couple with the end of the inlet tube at which the liquid phase enters the reactor. The impingement plate is positioned at a distance of a few centimeters from the end of the inlet.

A mixing and distribution device MD as shown schematically in FIG. 1 was constructed for a reactor R having a diameter of 1.7 m. The trough distributor comprised a main channel and 6 side channels having a height of 400 mm, with the sum of the base areas of the main channel and of the side channels being 60% of the total cross-sectional area of the reactor. 62 openings per $m^2$ having a diameter of 27 mm were located at the bottom of the trough-shaped channels, with an outlet tube having a diameter of 48 mm being installed at each opening and the length of the outlet tubes being selected so that the lower end of these was 150 mm above the distributor plate.

The distributor plate was provided with 100 nozzles per $m^2$ in triangular positions with the nozzles having a free diameter of 41.9 mm, a length of 320 mm above the distributor plate and of 150 mm below the distributor plate. Each of the nozzles was provided with an opening having a diameter of 24 mm at a height of 50 mm above the distributor plate for entry of the liquid phase and an opening having a diameter of 15 mm in the vicinity of the upper end of the nozzles for entry of the gaseous phase.

To assess the distribution behavior, water was fed to the mixing and distribution device. The water throughput was varied in the range from 100 $m^3/h$ to 540 $m^3/h$.

In all of the above load range, the mixing and distribution device squirted very little. No liquid flowed through the openings for entry of gas in the upper region of the nozzles.

In addition, the amount of water flowing through each nozzle of the distributor plate was measured. It was found that the amount flowing through in the load range from 300 to 540 $m^3/h$ varied very little between different nozzles, with a somewhat greater variation in the load range below 300 $m^3/h$, although the quality of liquid distribution was very high with a standard deviation of less than 5% in this load range, too.

The above-described reactor with mixing and distribution device was used for the selective hydrogenation of 1,3-butadiene in a C4 fraction to n-butenes.

Compared to carrying out the process in a reactor according to the prior art, the conversion based on 1,3-butadiene increased by 1% and the selectivity for the hydrogenation of 1,3-butadiene to n-butenes increased by 3%.

The invention claimed is:

1. A reactor for carrying out a three-phase reaction of a liquid phase, a gaseous phase and a catalyst arranged in a fixed catalyst bed, wherein the liquid phase and the gaseous phase being introduced from the outside the reactor and passed through the reactor in cocurrent from the top downward, wherein the reactor comprises:

a fixed catalyst bed being arranged horizontally in the reactor and a mixing and distribution device being arranged at the top of the reactor comprising:

a distributor plate with vertical nozzles, closed at the upper end, wherein from 50 to 200 nozzles per m2 are arranged regularly on the distributor plate and the nozzles have a free diameter of from 5 to 75 mm and a length of from 100 to 600 mm above the distributor plate and a length of from 20 to 250 mm below the distributor plate and having one or more openings for entry of the gaseous phase having a diameter of from 1 to 30 mm to provide a controlled pressure drop between entry into the reactor and entry into the vertical nozzles to be between 50 and 500 pascal and one or more openings, which are arranged below the one or more openings for entry of the gaseous phase, for entry of the liquid phase into the nozzles, with the number and size of the one or more openings for entry of the liquid phase being designed so that, at a predetermined liquid feed rate, the surface of the liquid on the distributor plate can be established below the one or more openings for entry of the gaseous phase and above the one or more openings for entry of the liquid phase, wherein the one or more openings for entry of the liquid phase have a diameter of from 3 to 35 mm and are arranged at a height of from 10 to 100 mm above the distributor plate and a trough distributor for the liquid phase wherein the liquid phase is introduced via an inlet tube into the trough distributor having trough-shaped channels and outlet tubes in the trough-shaped channels, and the length of the outlet tubes is designed in such a way that the lower ends thereof are positioned 20 to 200 mm above the distributor plate a port for introducing the gaseous phase separately from the liquid phase into a gas space between the trough distributor and the distributor plate, the port is arranged upstream of the distributor plate.

2. The reactor according to claim 1, wherein the number and size of the one or more openings in the nozzles of the distributor plate for entry of the liquid phase are designed so that the surface of the liquid on the distributor plate is established below the openings for entry of the gaseous phase and above the one or more openings for entry of the liquid phase even in the case of deviations of the liquid feed rate from the predetermined liquid feed rate by up to 20% in an upward direction and by up to 50% in a downward direction.

3. The reactor according to claim 1, wherein the reactor has a diameter in the range from 0.5 to 5 m.

4. The reactor according to claim 1, wherein from 70 to 150 nozzles per m2 are arranged regularly on the distributor plate.

5. The reactor according to claim 4, wherein the nozzles are arranged in triangular positions or in a square arrangement on the distributor plate.

6. The reactor according to claim 1, wherein the nozzles have a free diameter of from 10 to 60 mm and a length of from 200 to 400 mm above the distributor plate and a length of from 50 to 200 mm below the distributor plate and the one or more openings for entry of the liquid phase have a diameter of from 3 to 35 mm and are arranged at a height of from 22 to 75 mm above the distributor plate and the one or more openings for entry of the gaseous phase have a diameter of from 5 to 20 mm.

7. The reactor according to claim 6, wherein the nozzles have a free diameter of from 35 to 50 mm and a length of from 250 to 350 mm above the distributor plate and a length of from 100 to 150 mm below the distributor plate and the one or more openings for entry of the liquid phase have a diameter of from 10 to 25 mm and are arranged at a height of from 40 to 60 mm above the distributor plate and the one or more openings for entry of the gaseous phase have a diameter of from 7 to 15 mm.

8. The reactor according to claim 1, wherein the one or more openings for entry of the liquid phase can be adjusted in respect of their height and orientation.

9. The reactor according to claim 1, wherein the distributor plate is provided with no-load holes which are distributed uniformly over the distributor plate and whose number and size is selected so that in normal operation only a maximum of 5% of the total liquid phase passed through the reactor flows through the no-load holes.

10. The reactor according to claim 9, wherein the no-load holes have a diameter of from 10 to 20 mm.

11. The reactor according to claim 1, wherein the trough distributor is arranged from 10 to 300 mm above the upper end of the nozzles.

12. The reactor according to claim 1, wherein the trough-shaped channels of the trough distributor comprise a main channel and two or more side channels which are configured so that the liquid phase can flow unhindered between the main channel and the side channels.

13. The reactor according to claim 12, wherein the sum of the base areas of the main channel and the two or more side channels is from 30 to 70% of the total cross-sectional area of the reactor.

14. The reactor according to claim 1, wherein from 30 to 120 openings per m2 having a diameter of from 5 to 40 mm are provided at the bottom of the trough-shaped channels and an outlet tube having a diameter of from 15 to 75 mm is installed at each opening, with the length of the outlet tubes being set so that the lower ends of these are from 20 to 200 mm above the distributor plate.

15. The reactor according to claim 1, wherein the liquid phase is introduced into the reactor via an inlet tube and an impingement plate in the form of a disk with openings is arranged at the end of the inlet tube at which the liquid phase enters the reactor at a distance of a few cm from the end of the inlet tube.

* * * * *